United States Patent [19]

Lemieux et al.

[11] 4,137,401
[45] Jan. 30, 1979

[54] GLYCOSIDE-ETHER-ESTER COMPOUNDS

[75] Inventors: Raymond U. Lemieux, Edmonton; David R. Bundle, Ottawa; Donald A. Baker, Edmonton, all of Canada

[73] Assignee: Chembiomed Limited, Edmonton, Canada

[21] Appl. No.: 698,548

[22] Filed: Jun. 21, 1976

[30] Foreign Application Priority Data

Jul. 8, 1975 [GB] United Kingdom ............... 28729/75

[51] Int. Cl.$^2$ ............................................. C07H 13/06
[52] U.S. Cl. ..................................... 536/116; 424/11; 424/85; 536/4; 536/53; 536/115; 536/119
[58] Field of Search .................. 536/4, 115, 116, 119, 536/120, 53

[56] References Cited

U.S. PATENT DOCUMENTS

| | | | |
|---|---|---|---|
| 2,218,569 | 10/1940 | White | 536/4 |
| 3,356,674 | 12/1967 | Ikeda et al. | 536/4 |
| 3,655,645 | 4/1972 | Jacques | 536/116 |
| 3,729,461 | 4/1973 | Pomeranz et al. | 536/4 |
| 3,974,138 | 8/1976 | Lew | 536/4 |

OTHER PUBLICATIONS

Pigman, "The Carbohydrates", 1957, Academic Press Inc., New York, N. Y.; pp. 483–485.

Primary Examiner—Johnnie R. Brown
Attorney, Agent, or Firm—Alan A. Thomson

[57] ABSTRACT

Carbohydrate antigenic determinants containing a glycosidically linked bridging arm are synthesized and coupled to carrier molecules to form artificial antigens, and to solid supports to form immunoabsorbants. These artificial antigens are used to detect antibodies to the carbohydrate haptens, and to raise antisera specific for the carbohydrate antigenic determinants. The immunoabsorbants are used to purify or remove antibodies to the carbohydrate haptens. Specific examples are given to the synthesis of the Lewis-a, Lewis-b, B, and H(O) blood group antigens; to the preparation of antisera to these artificial antigens, and to the preparation of immunoabsorbants specific for antibodies to these antigens.

8 Claims, No Drawings

GLYCOSIDE-ETHER-ESTER COMPOUNDS

It is well known that carbohydrate structures of various complexities are the antigenic determinants for a wide range of substances. It has also been shown that it is possible to take relatively small molecules (haptens), which by themselves are devoid of antigenicity, and by linking them to a suitable high molecular weight carrier obtain an antigen which when administered to an animal under appropriate conditions will give rise to the production of antibodies having a specificity for the hapten. Thus, Goebel and Avery[1,2,3] showed that antibody specific for carbohydrate structures could be generated in experimental animals by immunizing them with artificial antigens prepared by the coupling of p-aminophenyl or p-aminobenzyl glycosides to protein. Canadian Pat. No. 966778 discloses that opium alkaloids covalently bonded to a protein molecule through a carboxy lower alkyl linking group are antigenic and these when administered to animals will give rise to the production of antibodies specific for the alkaloid. In both of the above examples the haptens must be linked to a carrier before they will show any antigenicity.

Heretofore there were two serious obstacles hindering the production of artificial carbohydrate antigens. The first was the difficulty in obtaining the antigenic determinant as very often these materials are only available in small amounts from natural sources. The Lewis-a trisaccharide antigenic determinant 2-acetamido-2-deoxy-4-O-(α-L-fucopyranosyl)-3-O-(β-D-galactopyranosyl)-D-glucopyranose, is a case in point. Prior to this invention no methods were available for the synthesis of a structure of this complexity, therefore, to obtain this compound it was necessary to isolate it from a rare natural source such as ovarian cyst fluid. From a single ovarian cyst, V. P. Rege et al.[4] were able to obtain 2.4 g of "dialysable products." After extensive manipulation about 10 mg of the Lewis-a trisaccharide antigenic determinant was isolated from this material. Similar difficulties have been encountered in obtaining the antigenic determinants of other human blood groups. At this point the second major difficulty arises, that is, properly functionalizing the carbohydrate antigenic determinant so that it can be utilized for the preparation of monospecific artificial antigens and immunoabsorbants.

Much ingenuity has been involved in the establishment of methods for the attachment of sugars to carrier polymers, however, all methods divulged to date have some serious drawbacks. Kabat and coworkers[5] have oxidized the reducing saccharide to aldonic acid which was subsequently attached to protein amino groups by way of a mixed anhydride. Unavoidably, this procedure results in the destruction of the terminal saccharide.

Conversion of the terminal saccharide to 1-(m-nitrophenyl) flavazole followed by reduction to the amine, diazotization and coupling to the protein has been used by Westphal and coworkers.[6] In addition to the destruction of the terminal saccharide, this method requires that the 2- and 3-positions of that saccharide be unsubstituted. Also, a new and highly antigenic structure is introduced in close proximity to the carbohydrate hapten and in addition, some sugars are sensitive to the conditions employed for diazotization. It is these last two difficulties which also limit the method of Goebel and Avery.[1,3]

SUMMARY OF THE INVENTION

It is the objective of the present invention to provide processes to chemically synthesize carbohydrate antigenic determinants in a form suitable for linkage to carrier molecules or solid supports. The invention further concerns the use of the products of the process for the following purposes:
 (a) preparation of artificial carbohydrate antigens.
 (b) preparation of antisera specific for the carbohydrate hapten of the artificial antigen.
 (c) preparation of immunoabsorbants (affinity absorbants) capable of selectively absorbing antibodies raised to either the artificial antigen or to natural antigens possessing the same terminal oligosaccharide structure as the antigenic determinant.

Particular reference is made to the lower oligosaccharide antigenic determinants of the human blood groups e.g., Lewis-a, Lewis-b, B and H(O).

Thus, according to the present invention there is provided a process for preparing a β-glycosyl plus bridging arm compound comprising:

reacting an activated sugar (a) selected from a glycosyl halide, a 1,2-orthoacyl ester derivative of a sugar, or a 1,2-oxazoline derivative of a sugar, with a monohydroxy carboxylic acid (b) of the general structure I, $$HO-R-COOR' \qquad I$$

where R is an aliphatic hydrocarbon thereof having from 3 to 17 carbon atoms and R' is a protecting group for the acid, to form a β-glycoside of the general structure II, $$\text{Sugar} \xrightarrow{\beta} O-R-COOR' \qquad II$$

and recovering said β-glycoside. The preparation of such a glycoside is the first claim and product of this invention.

As a further embodiment, the process is expanded to include the subsequent step of glycosidically linking in either the α- or β-anomeric configuration a further sugar to the initial sugar moiety to form a disaccharide of the general structure $$\text{Disaccharide} \xrightarrow{\beta} O-R-COOR' \qquad III$$

and recovering said disaccharide. This latter process may be further expanded with additional steps for the preparation of trisaccharides and tetrasaccharides of general structure IV and V, respectively, $$\text{Trisaccharide} \xrightarrow{\beta} O-R-COOR' \qquad IV$$

$$\text{Tetrasaccharide} \xrightarrow{\beta} O-R-COOR' \qquad V$$

and recovering said compounds as novel haptens.

In addition there is provided a process for the preparation of artificial antigens and immunoabsorbants by attaching the monosaccharide or lower oligosaccharide, plus bridging arm compound to a soluble carrier macromolecule or to an insoluble support. This is the final process step of this invention and yields the final products.

The production of antigenic determinants corresponding to structure types III, IV and V from the structure type II are outlined in typical reaction Schemes 1, 2 and 3 with reference to specific examples provided below.
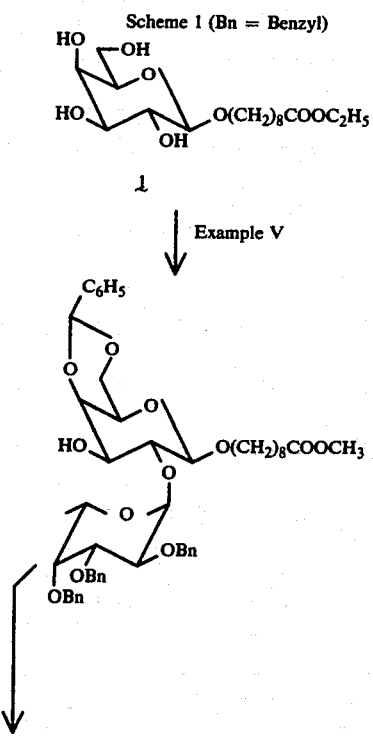
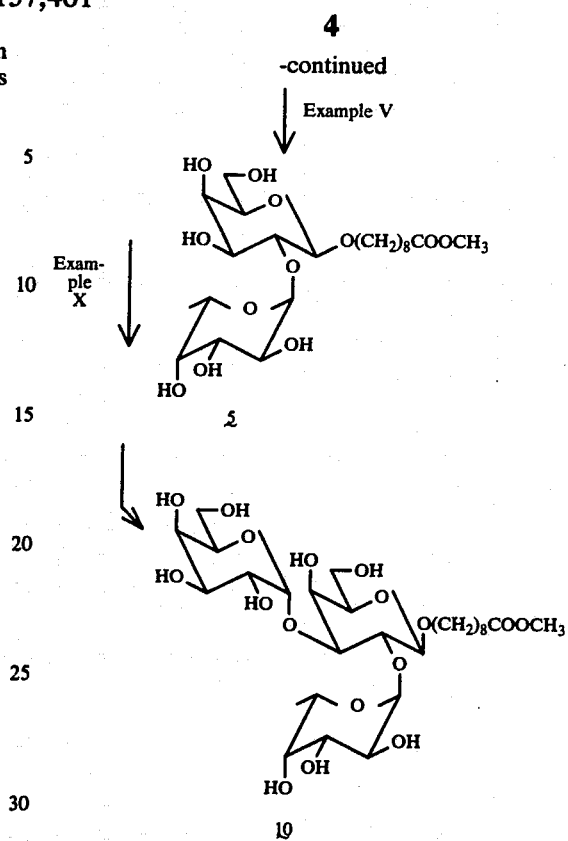
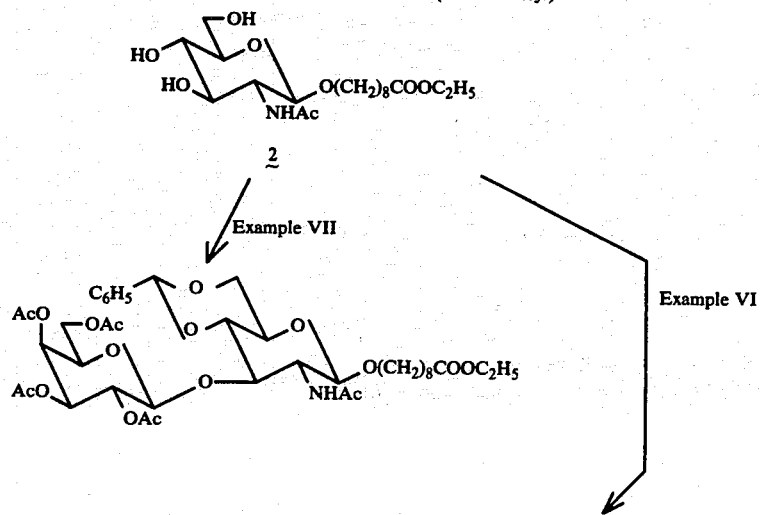

-continued
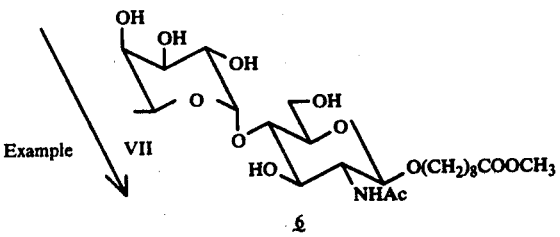
Example VIII ← Example VII
<u>6</u>
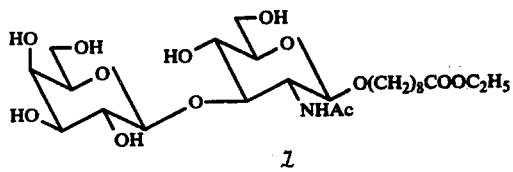
<u>7</u>
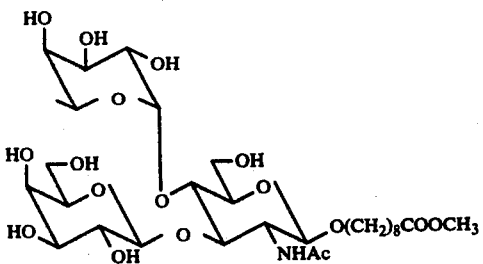
<u>8</u>
Scheme 3 (Ac = Acetyl, Bn = Benzyl)
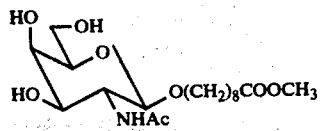
<u>3</u>
↓ Example IX

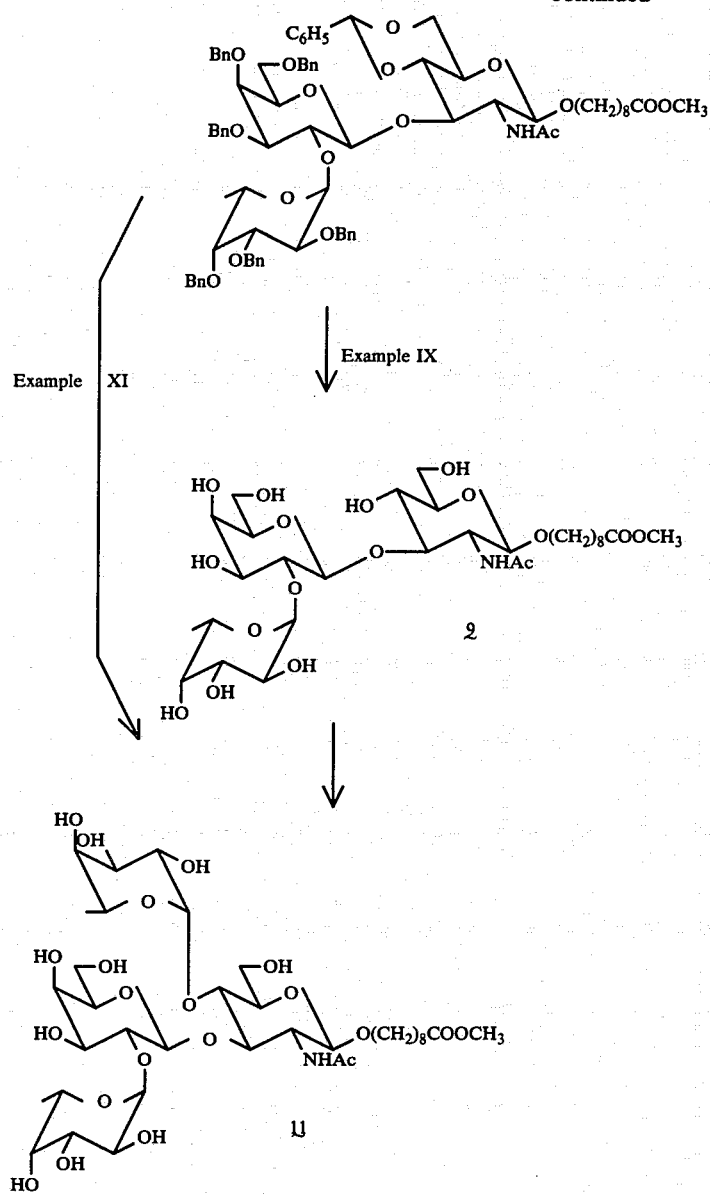

DETAILED DESCRIPTION

A detailed description of the present invention will now be given. Special reference will be made to the synthesis of the antigenic determinants for the human blood groups Lewis-a, Lewis-b, B and H(O) as examples, but the same techniques apply to other carbohydrate antigens. The overall process begins with the attachment of an appropriately selected sugar (for example 2-acetamido-2-deoxy-D-glucose (D-glcNAc) for the Lewis-a, b and H(O) determinants and D-galactose (D-gal) for the B determinant) by way of a β-glycosidic linkage to a protected monohydroxycarboxylic acid of general structure I.

HO—R—COOR'  I

The attachment is accomplished following procedures for the synthesis of β-glycosides well known in the art of carbohydrate chemistry and may follow β-glycosidation procedures such as the Koenigs-Knorr-Helferich-type methods using O-acetylated α-glycosyl halide derivatives of the sugar[13-16] or in the case of D-galactose by way of an O-acylated-1,2-orthoacyl ester derivative[17] and in the case of D-glucosamine by way of an O-acylated 1,2-oxazoline derivative[18] and, in each of the latter cases, the use of a suitable acid catalyst for promotion of the reaction. In this way the first products (structures II) of this invention are prepared.

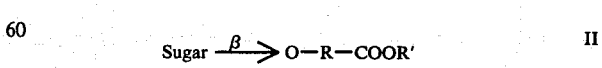

The aglycon (—O—R—COOR') of structure II is selected under the following conditions. The group R' is selected from the lower alkyl groups such as methyl, ethyl, n-propyl, isopropyl and n-butyl with some preference given to the methyl group for reasons of economy and generally more convenient reactivity of the methoxycarbonyl group over other alkoxycarbonyl groups. The —R— group provides a physical separation, a bridging arm, between the antigenic determinant and the carrier or support. This group should be inert towards the chemical reactions used for the further elaboration of the carbohydrate structure and is thereby effectively limited to structures that are aliphatic hydrocarbon in composition. The preferred structures correspond to that shown below, where n is in the range 3 to 17.

and the carbon chain is normal. Particularly useful are structures where the value of n is in the range 8-10 not only in view of the ready availability of the parent hydroxyacid but also because the inert rather featureless aliphatic chain appears to function as an internal adjuvant. Thus, higher antibody titres are obtained using bridging arms of this length as opposed to those of shorter length. Most examples in this invention utilize —R— equal to —$C_8H_{16}$— since with this grouping very high titer antisera were consistently achieved.

The β-glycoside derivative products will have the general structure

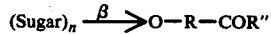

where R is an aliphatic hydrocarbon moiety having 3 to 17 carbon atoms and R" is —H, —OH, —$NH_2$, —$NHNH_2$, —$N_3$, —O—alkyl or —O—aryl, and n has a value of 1 to 4. Thus the (Sugar)$_n$ $\overset{\beta}{\rightarrow}$ O—R—COOR' where R' is a protecting group, may be converted to the product (Sugar)$_n$ $\overset{\beta}{\rightarrow}$ O—R—COR" where the R" may constitute other than a protecting group. The initial protecting group —OR' e.g. the methyl, ethyl, propyl and butyl esters, may be replaced with other R" groups either to form alternative haptens for a particular application or to facilitate coupling to a carrier or support.

The following four specific preparations exemplify the preparation of compounds of structure II. In all cases, the structures achieved were substantiated by modern methods of chemical analysis including carbon-13 and proton nuclear magnetic resonance spectra (cmr and pmr, respectively), elemental analysis and in many instances by high-resolution mass spectrometry.

EXAMPLE I

The antigenic determinant 8-methoxycarbonyloctyl β-D-galactopyranoside (1).

8-Methoxycarbonyl-1-octanol (21.4 g, 0.115 mole) and dried mercuric cyanide (30.3 g, 0.119 mole) were dissolved in a 1:1 mixture of dry distilled benzene-nitromethane (850 ml). The solution was stirred and 200 ml of solvent was distilled. Mixed solvent (200 ml) was added and calcium sulfate (40 g) was added followed by 2,3,4,6-tetra-O-acetyl-α-D-galactosyl bromide (38.7 g, 0.094 mole). The mixture was stirred at room temperature for 36 h and then heated at 70° for 2 h. After cooling, the solution was filtered and the filtrate evaporated in vacuo to give a yellow syrup. This syrup was dissolved in distilled ethyl acetate (500 ml) and the solution was washed with an aqueous solution (10% w/w, 500 ml) of sodium iodide. The organic phase was then washed successively with a saturated solution of sodium thiosulphate (200 ml) and $H_2O$ (2 × 250 ml). The organic phase was dried over sodium sulphate and then evaporated in vacuo after filtration. This syrup (~50 g) after drying under high vacuum overnight was dissolved in dry distilled methanol (200 ml) and to this solution, 200 ml of methanolic sodium methoxide (150 mg of sodium) was added. After stirring at room temperature for 24 h, acid resin (prewashed a few times in methanol) was added and stirred until the pH was neutral. After filtration, the solution was evaporated and the waxy residue dissolved at room temperature in 100 ml of $H_2O$. This solution was extracted with ether (2 × 40 ml) and then placed in the fridge. Upon standing, crystallization occurred. The white crystals were filtered and dried. Weight 13.5 g (41%), mp 104°–105°, $[\alpha]_D^{25}$ − 13.4° (c 1, 95% ethanol).

EXAMPLE II

The antigenic determinant 8-ethoxycarbonyloctyl 2-acetamido-2-deoxy-β-D-glucopyranoside (2).

Mercuric cyanide (31.8 g, 126 mmol) and anhydrous calcium sulfate were added to a solution of 8-ethoxycarbonyl-1-octanol (25 g, 124 mmol) in 100 ml of dry benzene. The mixture was protected from moisture while stirring for 1 h at room temperature prior to addition of 2-acetamido-3,4,6-tri-O-acetyl-2-deoxy-α-D-glucopyranosyl chloride (25 g, 68 mmol). The mixture was efficiently stirred for 4 days at room temperature. Dichloromethane (400 ml) was added, the solids were removed by filtration, and the filtrate was sequentially washed with 10% aqueous sodium chloride solution (50 ml), once with saturated aqueous sodium bicarbonate solution (25 ml), and twice with water (50 ml). In each case, the aqueous layer was back-extracted with a little dichloromethane. After drying over magnesium sulfate, the solvents were removed to leave a syrup which crystallized from a mixture of diethyl ether and n-hexane. The crude yield of 8-ethoxycarbonyloctyl 2-acetamido-3,4,6-tri-O-acetyl-2-deoxy-β-D-glucopyranoside was 28.9 g (80%). A recrystallized sample showed mp 112°, $[\alpha]_D^{20}$ − 12.2° (c 2.4, chloroform). De-O-acetylation of this compound with triethylamine (27 ml) in methanol (500 ml) at 0°–5° for 18 h gave after evaporation of the solvent compound 2 as a chromatographically homogeneous powder which resisted crystallization and was therefore characterized as its hydrazide derivative mp 200°–201°, $[\alpha]_D^{26}$ − 22.5° (c 1, water), prepared by treating 2 with an 85% solution of hydrazine hydrate.

An alternate preparation of the antigenic determinant 2.

A mixture of p-toluene sulfonic acid (10 mg), 8-ethoxycarbonyl-1-octanol (1 g), 2-methyl-4,5-(3,4,6-triacetyl-2-deoxy-α-D-glucopyrano)-Δ²-oxazoline (1 g) was dissolved in 10 ml of a 1:1 mixture of benzene and nitromethane and refluxed for 3 hours. The usual workup gave 8-ethoxycarbonyloctyl 2-acetamido-3,4,6-tri-O-acetyl-2-deoxy-β-D-glucopyranoside (1.28 g, 79%). De-O-acetylation as described in example II gave the title antigenic determinant in 90% yield.

EXAMPLE III

The antigenic determinant 8-methoxycarbonyloctyl 2-acetamido-2-deoxy-β-D-glucopyranoside (3).

Compound 3 was prepared as described in example VI below.

EXAMPLE IV

The antigenic determinant 5-methoxycarbonylpentyl 2-acetamido-2-deoxy-β-D-glucopyranoside (4).

Condensation of 2-acetamido-3,4,6-tri-O-acetyl-2-deoxy-α-D-glucopyranosyl chloride with 5-ethoxycarbonyl-1-pentanol under the same conditions as reported in example II gave a 74% yield of 5-ethoxycarbonylpentyl 2-acetamido-3,4,6-tri-O-acetyl-2-deoxy-β-D-glucopyranoside, mp 101°–102°, $[\alpha]_D^{25}$ − 16.8° (c 1.06, chloroform). De-O-acetylation of this compound using sodium methoxide gave after crystallization a 92% yield of 4 mp 154°–155° (melts and resolidifies) remelts 167°, $[\alpha]_D^{18}$ − 25.5° (c 1.1, water).

The spirit and scope of this invention encompasses the use of compounds of general structure II for the elaboration of more complex antigenic determinants. In such processes, additional sugars are added to appropriately blocked derivatives of II using synthetic methodologies known to carbohydrate chemistry. In this fashion, structures of type III are achieved wherein a disaccharide unit is present in contrast to the simple monosaccharide units in II.

III

Examples V, VI, and VII illustrate the preparation of compounds of general structure III.

EXAMPLE V

The antigenic determinant 8-methoxycarbonyloctyl 2-O-(α-L-fucopyranosyl)-β-D-galactopyranoside (5).

To a colorless solution of 6.6 g of α,α-dimethoxytoluene (0.043 mole) in 60 ml of distilled acetonitrile, p-toluenesulfonic acid (0.285 g, recrystallized) was added. The solution instantaneously became yellow and immediately 8-methoxycarbonyloctyl β-D-galactopyranoside (10 g, 0.028 mole) was added. The yellow color disappeared within 5 minutes and dissolution took place in 30 minutes. The solution, protected from humidity, was stirred at room temperature for 44 hours. At this time, no starting material was detectable by thin layer chromatography (tlc) and a new product 8-methoxycarbonyloctyl 4,6-O-benzylidene-β-D-galactopyranoside was present. The presence of the isomeric 3,4-O-benzylidene analog of this compound could not be detected by tlc. A few drops of triethylamine were added (pH ~7) and the solvent was evaporated. Toluene was added to the residual syrup and then evaporated in vacuo and this operation was repeated once more. The white waxy solid was then stirred overnight with hexane (distilled) to remove a fast running uv absorbing spot, and a very fine powder was obtained. After filtration, the solid was dissolved in dichloromethane (distilled, 500 ml) and the solution washed with a saturated sodium bicarbonate solution (100 ml) and then water (300 ml). After drying over sodium sulfate, the organic phase was evaporated to dryness to give the pure 4,6-benzylidene derivative. The product in solution in methanol was placed in a dessicator containing n-pentane for crystallization. The yield of recrystallized product was 83%, mp 127°–128°, $[\alpha]_D^{25}$ −33° (c 1, chloroform). A portion of the benzylidinated compound (7 g, 0.016 mole) was dissolved in 400 ml of dry distilled dichloromethane containing 10 ml of pyridine (distilled). The solution was cooled to −40° and 2 ml (0.017 mole) of distilled benzoyl chloride was added dropwise. After 2 h at that temperature tlc examination showed the presence of only one product, 8-methoxycarbonyloctyl 3-O-benzoyl-4,6-O-benzylidene-β-D-galactopyranoside. Ice chips were added and the solution was poured in a mixture of water and ice (300 ml) vigorously stirred. The organic phase was separated and the aqueous phase back-extracted with dichloromethane (2 × 100 ml). The combined organic phase was washed with a saturated sodium bicarbonate solution (200 ml) and then with water (2 × 300 ml). After drying over sodium sulphate, the organic phase was evaporated to dryness. The remaining pyridine was co-evaporated with toluene in vacuo to give 8.7 g (100%) of the desired blocked galactopyranoside. Recrystallization was achieved by dissolving the syrup in 2-propanol and the solution was placed in a desiccator containing n-pentane. The yield was quantitative, mp 96°–97°, $[\alpha]_D^{25}$ + 60.5° (c 1, chloroform).

The above selectively blocked galactopyranoside (4 g, 7.38 mmol) was dissolved in a mixture of purified dichloromethane (10 ml) and distilled N,N-dimethylformamide (0.62 ml) containing 1.6 g (10.7 mmol) of tetraethylammonium bromide and 7.8 g of diisopropylethylamine. To the solution tri-O-benzyl-α-L-fucosyl bromide (freshly prepared from 20.8 mmol of tri-O-benzyl-1-p-nitrobenzoyl-α-L-fucopyranose) was added, followed by addition of 2 g of molecular sieves 4Å. After 48 h the reaction mixture was diluted with dichloromethane (40 ml) and the solids were removed by filtration. The filtrate was washed with water and dried over sodium sulphate. After filtration, the solution was evaporated in vacuo to a pale yellow syrup. This syrup was dissolved in ether-ethyl acetate (3:2) and applied to an alumina column. The products were rapidly eluted with the same solvent system and obtained as a pale yellow syrup upon evaporation of the solvents. This syrup was dissolved in hexane-ethyl acetate (8:2) and applied to a silica gel (200 g) column. The elution was performed using the same solvent mixture. Two fast running spots were eluted first, then the desired compound. The weight (after being dried under high vacuum) was 6.1 g (86%).

De-O-benzoylation with methanolic sodium methoxide gave 8-methoxycarbonyloctyl 4,6-O-benzylidene-2-O-(tri-O-benzyl-α-L-fucopyranosyl)-β-D-galactopyranoside in 80% yeild, mp 104°–105°, $[\alpha]_D^{25}$ − 54° (c 1, chloroform). Hydrogenation over 5% palladium on charcoal gave the title compound 5 as a tlc homogeneous syrup which was characterized as its hydrazide derivative, mp 178° (ethanol-ether), $[\alpha]_D^{18}$ −87.4 (c 1.02, water).

EXAMPLE VI

The antigenic determinant 8-methoxycarbonyloctyl 2-acetamido-2-deoxy-4-O-(α-L-fucopyranosyl)-β-D-glucopyranoside (6).

Sodium (18 mg) was added to dry methanol (40 ml) and after the reaction was complete 8-ethoxycarbonyloctyl 2-acetamido-3,4,6-tri-O-acetyl-2-deoxy-β-D-glucopyranoside (1.06 g, 2 mmol) was added. The solution was kept at room temperature for 24 h prior to deionization using the acid resin. Solvent removal left 753 mg of the de-O-acetylated product which was not characterized but used directly for the preparation of the title compound. The material, dried in vacuo over phosphorus pentoxide, was dissolved in DMF (5 ml)

which contained α,α-dimethoxytoluene (2 ml) and p-toluenesulfonic acid (25 mg). After heating at 40° for 1.5 h, the solution was cooled and triethylamine added to neutralize the acid. After solvent removal, toluene (5 ml) was added and removed by evaporation. This procedure was repeated twice and the residue then triturated with hexane (10 ml). The solid was collected and dissolved in dichloromethane (25 ml). The solution was washed three times with water (5 ml), dried over magnesium sulfate, and evaporated to a residue which crystallized from ethanolpetroleum ether. The yield of 8-methoxycarbonyloctyl 2-acetamido-4,6-O-benzylidene-2-deoxy-β-D-glucopyranoside was 481 mg (50%), mp 219°. Recrystallization gave the analytical sample, mp 221°, $[\alpha]_D^{25} - 56°$ (c 1.3, dimethylformamide).

This compound was acetylated using a 1:1 mixture of acetic anhydride and pyridine for 24 h. The product was isolated in the usual manner and de-O-benzylidinated using 50% acetic acid at 100° for 25 min to yield 2-acetamido-3-O-acetyl-2-deoxy-β-D-glucopyranoside, mp 122°–123°, $[\alpha]_D^{30} - 47.3$ (c 1.1, chloroform).

The 6-position of this compound was selectively benzoylated in 88% yield by treatment with 1.1 equivalents N-benzoylimidazole. A mixture of the above 6 benzoate, 8-methoxycarbonyloctyl 2-acetamido-3-O-acetyl-6-O-benzoyl-2 2-deoxy-β-D-glucopyranoside, mp 105°, $[\alpha]_D^{32} - 42.0°$ (c 1, chloroform), (1.55 g, 2.9 mmol) tetraethylammonium bromide (630 mg, 3 mmol), diisopropylethylamine (450 mg) and DMF (4 ml) in dichloromethane 20 ml was added to 2,3,4-tri-O-benzyl-α-L-fucopyranosyl bromide freshly prepared from 3.38 g, 5.8 mmol, of 2,3,4-tri-O-benzyl-1-O-p-nitrobenzoyl-β-L-fucopyranose. The solution was stirred at room temperature for three days after which time tlc examination no longer showed the presence of any starting material. Dichloromethane (150 ml) was added and the solution was washed in the usual manner with water and aqueous sodium bicarbonate solution prior to solvent removal.

The syrupy product was used directly for the preparation of 8-methoxycarbonyloctyl 2-acetamido-4-O-(2,3,4-tri-O-benzyl-α-L-fucopyranosyl)-2-deoxy-β-D-glucopyranoside. The crude disaccharide (3.78 g) was dissolved in 50 ml of dry methanol, and 5 ml of 0.2 N sodium methoxide in methanol was added. After 24 h at room temperature, the solution was deionized using the acid resin. Solvent removal left an oil which was dissolved in dichloromethane (100 ml). The solution was washed with water and dried over magnesium sulfate prior to evaporation to a residue (1.01 g, 85% yield) from the fully blocked disaccharide. Purification was by recyrstallization from ethyl acetate-hexane, mp 145°–146°, $[\alpha]_D^{25} - 33.6°$ (c 1.2, chloroform).

Hydrogenation of this compound in ethanol over 5% palladium on charcoal at 50 psi and 70° for 3 days gave after removal of the solvent and catalyst compound 6 as an amorphous solid, $[\alpha]_D^{25} - 95.5°$ (c 1.0, water) in 97% yield.

EXAMPLE VII

The antigenic determinant 8-Ethoxycarbonyloctyl 2-acetamido-2-deoxy-3-O-(β-D-galactopyranosyl)-β-D-glucopyranoside (7).

Compound 2 (6.3 g, 15.5 mmol) was added to a stirred solution of anhydrous zinc chloride (7.0 g) in freshly distilled benzaldehyde (100 ml) to which was added an anhydrous calcium sulfate (14 g). After 20 h at room temperature, the solids were removed by filtration. The addition of hexane (500 ml) to the filtrate caused the precipitation of a gummy precipitate which was triturated several times with hexane. The residue was then triturated with pyridine (7 ml) prior to the addition of dichloromethane (300 ml). The resulting solution was washed twice with water (25 ml), twice with saturated aqueous sodium bicarbonate solution (25 ml), and twice again with water (25 ml). Solvent removal, after drying over sodium sulfate, left a residue which crystallized from ethanol (4.68 g, 61% yield), mp 210°–220°. The melting point was unchanged by recrystallization from aqueous methanol, $[\alpha]_D^{24} - 55.5°$ (c 1.3, chloroform).

A solution of this compound (12.1 g, 24.5 mmol) and mercuric cyanide (7.35 g, 30 mmol) in 1600 ml of a 1:1 mixture of benzene and nitromethane was distilled at atmospheric pressure to remove 100 ml of solvent. Calcium sulfate (40 g) and tetra-O-acetyl-α-D-galactopyranosyl bromide (12.3 g, 29.6 mmol) were added, after cooling, and the temperature was then maintained at 50° for 20 hours. Tetra-O-acetyl-galactosyl bromide (10 g, 24.4 mmol), mercuric cyanide (6.15 g), and calcium sulfate (10 g) were then added, and the mixture was stirred a further 20 h at 50°. TLC examination indicated the absence of the monosaccharide alcohol. The solids were removed by filtration and washed with dichloromethane (800 ml). The combined filtrates were twice washed with 30% aqueous potassium iodide solution (50 ml), twice with saturated aqueous sodium bicarbonate solution (50 ml), and then twice with water (50 ml). After drying over sodium sulfate, the solvent was removed to leave a syrup. The syrup was dissolved in a little hot ethanol and diethyl ether then added to near turbidity. The addition of petroleum ether caused the precipitation of a solid which was crystallized from ethyl acetate-hexane (17.1 g, 85%, mp 108–109°). Recrystallization from ethyl acetate-diethyl ether afforded pure material, mp 110°–111°, $[\alpha]_D^{27} - 8.2°$ (c 1.4, chloroform). Removal of the hydroxyl protecting groups in the manner described in previous examples gave 7 in 82% yield as a white solid, mp 207°–208°. Recrystallization from methanol raised the melting point to 211°–212°, $[\alpha]_D^{17} - 22°$ (c 1, water).

Appropriately blocked derivatives of compounds of structure-type III and encountered in the preparations of compounds 5, 6 and 7 are used to elaborate by way of chemical synthesis structures of type IV,

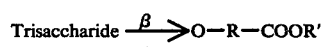
                                                                   IV Thus, the terminal trisaccharide IV units of important human blood group antigens are obtained. This is exemplified by the following preparations of the antigenic determinants for the Lewis-a, O(H) and B Human blood groups, in Examples VIII, IX and X respectively.

EXAMPLE VIII

The antigenic determinant 8-methoxycarbonyloctyl 2-acetamido-2-deoxy-4-O-(α-L-fucopyranosyl)-3-O-(β-D-galactopyranosyl)-β-D-glucopyranoside (8).

8-Ethoxycarbonyloctyl 2-acetamido-3-O-(tetra-O-acetyl-β-D-galactopyranosyl)-4,6,-O-benzylidene-2-deoxy-β-D-glucopyranoside (7.65 g) (cf example VII) was de-O-benzylidinated using aqueous acetic acid under conditions similar to those used in example VI to give 5.6g (81%) of product, mp 153.5°, $[\alpha]_D^{16} + 9.6°$ (c 1.4, chloroform). A portion of this material (1.47 g, 2 mmol) was selectively acetylated at the 6-position using N-acetyl imidazole (2.2 mmol) to yield 1.10 g (71%) of 8-ethoxycarbonyloctyl 2-acetamido-6-O-acetyl-3-O-(tetra-O-acetyl-$\beta$-D-galactopyranosyl)-2-deoxy-$\beta$-D-glucopyranoside, as a tlc homogeneous syrup, $[\alpha]_D^{31}$ + 6.2° (c 1, chloroform).

A mixture of this compound (3.0 g, 3.86 mmol), tetraethylammonium bromide (840 mg, 4 mmol), diisopropylethylamine (600 mg, 4.64 mmol), dichloromethane (25 ml), and DMF (5 ml) was added to tri-O-benzyl-fucosyl bromide (2.56 g, 5.15 mmol) dissolved in dichloromethane (5 ml) and DMF (1 ml) was then added, and the solution was stirred for an additional 3 days. Dichloromethane (300 ml) was added, and the product was isolated in the usual manner. Purification was effected by chromatography on a silica gel column (75 × 3.5 cm). Development with 1:1 ethyl acetatehexane (300 ml) was followed by the same solvent but to which 5% ethanol was added. The first band to appear soon after changing solvent provided the blocked trisaccharide as a tlc homogeneous syrup (4.36 g, 94%), $[\alpha]_D^{22}$ − 54° (c 1.1, chloroform). Removal of the hydroxyl protecting groups by methods similar to those already described gave the desired antigenic determinant 8 as an amorphous solid, $[\alpha]_D^{25}$ − 73.5° (c 1, water).

EXAMPLE IX

The antigenic determinant 8-methoxycarbonyloctyl 2-acetamido-2-deoxy-3-O-(2-O-[$\alpha$-L-fucopyranosyl]-$\beta$-D-galactopyranosyl-$\beta$-D-glucopyranoside (9).

A solution of 8-methyoxycarbonyloctyl 2-acetamido-4,6-O-benzylidene-2-deoxy-$\beta$-D-glucopyranoside (480 mg, 1 mmol) (cf example VI) and mercuric cyanide (304 mg, 1.2 mmol) in 50 ml of a 1:1 mixture of benzene and nitromethane was distilled at atmospheric pressure to remove 10 ml of solvent. Powdered calcium sulfate (1.5 g) and the bromide (prepared from 900 mg of 3,4,6-tri-O-benzyl-1,2-di-O-p-nitrobenzoyl-$\beta$-D-galactopyranose) in 5 ml of a 1:1 benzene nitromethane mixture were added after cooling, and the temperature then maintained at 40° for 36 h. Tlc examination at this point indicated that no bromide remained. The reaction mixture was diluted with dichloromethane (25 ml), filtered and the filter cake washed with dichloromethane (3 × 10 ml). The combined filtrate and washings were made up to 200 ml with dichloromethane and washed with 30% aqueous potassium iodide (10 ml), saturated sodium bicarbonate solution (10 ml) and water (2 × 10 ml). After drying over sodium sulfate the solvent was removed leaving a syrup which was dissolved in a small amount of dichloromethane and applied to a column of silica gel D-O (65 g). The column was first developed with a mixture of benzene-ethyl acetate (4:1) and then the product was eluted with a 2:1 benzene-ethyl acetate mixture. Solvent removal afforded 550 mg (52%) of the blocked disaccharide which was crystallized from ethanol, mp 152°-153°, $[\alpha]_D^{24}$ + 42.0° (c 1.1, chloroform).

This disaccharide (400 mg) was suspended in 40 ml anhydrous methanol containing 12 mg sodium and the reaction mixture stirred for 24 h at room temperature. The solution was de-ionized with acid resin and the residue obtained after evaporation of the solvent was dissolved in benzene and applied to a 4 g column of silica gel D-O. After washing the column with benzene to remove the methyl p-nitrobenzoate the product was eluted with benzene-ethyl acetate 2:1. Evaporation of the eluent afforded 260 mg (78%) of the de-O-p-nitrobenzoylated compound as a tlc homogeneous syrup.

To a mixture of this compound (1.03 g, 1.13 mmol), tetraethylammonium bromide (317 mg, 1.5 mmol), diisopropylethylamine (194 mg, 1.5 mmol) molecular sieves 4Å (1 g), dichloromethane (8 ml) and dimethylformamide (0.6 ml) was added 2,3,4-tri-O-benzyl-$\alpha$-L-fucopyranosyl bromide freshly prepared from 2,3,4-tri-O-benzyl-1-O-p-nitrobenzoyl-$\beta$-L-fucopyranose (1.459 g, 2.5 mmol) in dichloromethane (2 ml). After 4 days tlc examination showed that no starting material remained, 200 μl of methanol were then added and after 2 h the reaction mixture was diluted with 25 ml dichloromethane and filtered. The filtrate was made up to 100 ml with dichloromethane and washed in the usual manner with water and aqueous saturated sodium bicarbonate prior to solvent removal. Chromatography of the crude product on silica gel D-O using ethyl-acetate-hexane 1:1 as eluent gave the fully blocked trisaccharide (1.116 g, 74% of theoretical) as a tlc (benzene-ethyl acetate 2:1) homogeneous syrup.

A solution of this compound (890 mg) dissolved in 9 ml of dichloromethane containing 1.0 ml of 90% trifluoroacetic acid was allowed to stand at room temperature for 10 minutes. The reaction mixture was diluted with toluene (10 ml) and water (0.5 ml) and the solvents evaporated. Chromatography of the crude product on silica gel gave after crystalliaztion from ethyl acetate-pentane 530 mg (64% of theoretical yield) of the de-O-benzylidinated trisaccharide, mp 125°-126°, $[\alpha]_D^{24}$ − 37.4° (c 1.1, chloroform).

To a solution of this compound (452 mg) in ethanol (7 ml) was added 300 mg of 5% palladium on charcoal and the mixture shaken under a 100 psi atmosphere of hydrogen for 36 hr. The catalyst was removed by filtration and washed with three 10 ml portions of hot ethanol. The combined filtrate and washings were evaporated and the product was dissolved in a small amount of water and freeze dried. The crude product 9, (255 mg, quantitative yield) was homogeneous by tlc (isopropanol-ammonium hydroxide-water 7:1:2) and crystallized from a mixture of methanol and ether, mp 195°, $[\alpha]_D$ − 60.3° (c, 1.1, water).

EXAMPLE X

The antigenic determinant 8-methoxycarbonyloctyl 2-O-($\alpha$-L-fucopyranosyl)-(3-O-$\alpha$-D-galactopyranosyl)-$\beta$-D-galactopyranoside (10).

8-Methoxycarbonyloctyl 3-O-benzoyl-4,6-O-benzylidene-2-O-(tri-O-benzyl-$\alpha$-L-fucopyranosyl)-$\beta$-D-galactopyranoside (5 g, 5.2 mmol) (cf example V) in 250 ml of a freshly prepared methanolic sodium methoxide solution (1%) was stirred at room temperature for 2 h at which time the reaction was complete as judged by tlc. Sufficient acid ion exhange resin, prewashed with methanol, was added to neutralize the solution (pH ≈7). The resin was removed by filtration and the filtrate evaporated in vacuo to give a pale yellow syrup (≈4.3 g). Crystallization from ethanol hexane gave 3.55 g (80%) of crystalline de-O-benzolyated compound, mp 104°-105°, $[\alpha]_D^{25}$ − 54° (c 1, chloroform).

This compound (0.6 g, 0.7 mmol) was dissolved in dichloromethane (0.66 ml) and N,N-dimethylformamide (0.06 ml) containing tetraethylammonium bromide (0.16 g, 1 mmol), Hünigs base (0.27 g) and molecular sieve 4Å (1 g). Freshly prepared tetra-O-benzyl-$\alpha$-D-galactopyranosyl bromide (1.04 g, 1.7 mmol) in a small amount of dichloromethane was then added and the reaction mixture was then stirred at room temperature for 48 hours. An additional portion (0.5 g, 0.85 mmol) of the bromo sugar was then added and the reaction mixture stirred for a further 24 hours. The reaction mixture was diluted with dichloromethane and the solids were removed by filtration. The filtrate was washed with water and dried over sodium sulphate. After filtration the solution was evaporated to a syrup. This syrup was purified by rapid chromatography on an alumina column before being applied to a silica gel column. Elution was obtained with ethyl acetate-hexane (2:8) and the desired blocked trisaccharide obtained pure by pooling the appropriate fraction. The yield was 0.686 g (71%), mp 82°–83° (recrystallized from heptane-ether).

To a solution of the above compound (600 mg, 0.43 mmol) in ethanol (10 ml) containing ethyl acetate (1 ml) was added 350 mg of 5% palladium on charcoal and the mixture was shaken under hydrogen at a pressure of 100 psi (gauge pressure) for 5 days. The catalyst was filtered off and washed with hot ethanol (3 × 5 ml). The combined filtrates were evaporated in vacuo to give compound 10 (177 mg, 62%). A portion was recrystallized from methanol-ether, mp 147°–150°.

Elaboration of appropriately blocked derivatives of structure type IV give tetrasaccharides of general structure type V.

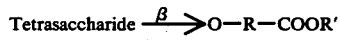

V

Thus, the terminal tetrasaccharide antigenic determinant of the human blood group Lewis-b is obtained as illustrated by Example XI.

EXAMPLE XI

The antigenic determinant 8-methoxycarbonyloctyl 2-acetamido-2-deoxy-4-O-($\alpha$-L-fucopyranosyl)-3-O-(2-O-[$\alpha$-L-fucopyranosyl]-$\beta$-D-galactopyranosyl)-$\beta$-D-glucopyranoside (11).

8-Methoxycarbonyloctyl 2-acetamido-3-O-(3,4,6-tri-O-benzyl-2-O-[2,3,4-tri-O-benzyl-$\alpha$-L-fucopyranosyl]-$\alpha$-D-galactopyranosyl)-2-deoxy-$\beta$-D-glucopyranoside (620 mg, 0.5 mmol) (cf example IX) was selectively acetylated at the 6-position of the N-acetyl glucosamine residue by treatment with N-acetyl imidazole (0.6 mmol). $\alpha$-Fucosylation of the compound as in example VIII gave the desired blocked tetrasaccharide in 70% yield as a tlc homogeneous syrup. Removal of the hydroxyl protecting groups by the methods previously described (cf example VIII) gave tetrasaccharide 11 in 80% yield.

The products obtainable through the general procedures embodied in this invention arise from the novel concept of exploring applications of synthetic carbohydrate chemistry toward the elaboration of antigenic determinants in the form of structure-types II, III, IV and V for use not only as inhibitors of antibody-antigen interactions but, and especially, for use as reagents for the preparation of highly effective artificial antigens and immunoabsorbants which show promise of a wide range of useful application.

The demonstration that synthesis can lead to large scale preparations of important natural carbohydrate determinants means that mankind will no longer be dependent on rare and expensive sources of minute amounts of these determinants. The demonstration that these determinants can be produced in such a fashion and that these are readily employable for the preparation of effective highly immunogenic antigens promises to be of great utility for the provision of antibodies which are monospecific for the selected determinant. Thus, applications for the provision of typing sera for both blood sera and cells are indicated and demonstrated. Extension to the typing of tissues is evident and is expected to be of major utility for the proper matching of tissues for tissue transplantation operations. Antibodies raised against the wide range of carbohydrate determinants arising from the disclosure of this invention can serve as diagnostic reagents and in the preparation of affinity columns as now widely practiced using so-called lectins which are natural proteins possessing specific affinity for a carbohydrate structure. Of major importance is the provision of antisera specific to minor human blood groups such as Le$^a$ and Le$^b$. Effective typing sera for such minor groups are presently rare and expensive but their diagnosis is of increasing importance due to increasing likelihood in modern medicine of multiple blood transfusions and the hazard thus raised of a recipient having, unknowingly, been previously sensitized.

The demonstrations contained in this invention show that the synthesized determinants can be used for the preparation of highly effective monospecific immunoabsorbants. These immunoabsorbants promise to have important and wide utility for the removal of undesired antibodies from blood sera and for the isolation and purification of specific antibodies through absorption-desorption procedures. in this latter regard, the utility of incomplete determinants for the preparation of affinity chromatograms is of substantial significance since the use of complete determinants can lead to binding of the antibodies that is so strong that the desorption cannot be accomplished without extensive denaturation of the antibody and, thereby, loss of its specificity.

The above-mentioned benefits accruing as the result of the discoveries leading to this invention are demonstrated by Examples XII to XIX presented below. These examples were selected from a large list of similar investigations leading to this invention and were chosen so as to well establish the spirit and scope of the invention in terms of the utility of determinants and carrier molecules to prepare artificial antigens and of determinants and solid supports to prepare immunoabsorbants.

The attachments of the determinants beginning with the ester grouping contained in the structure-types II, III, IV and V can be made following several procedures well known to this area of investigation. The most direct way is by straightforward aminolysis of the ester on the bridge-in arm using dry methanol as solvent,

—COOCH$_3$ + H$_2$N— → —CONH— + CH$_3$OH the amide grouping serving as the linkage between hapten and carrier or solid support.

A second method comprises first converting the ester to the free carboxylic acid followed by condensation of the acid with amino groups using suitable condensing agents such as dicyclohexyl and other carbodiimides or 1-ethoxy-carbonyl-2-ethoxy-1,2-dihydroquinoline (EEDQ),

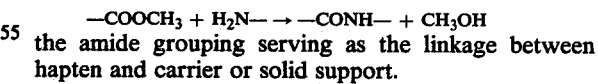

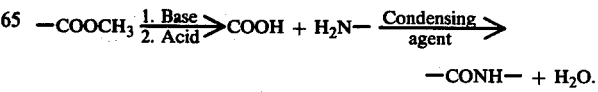

—CONH— + H$_2$O.

A third method (and that preferred) involves conversion of the ester to hydrazide followed by nitrous acid oxidation of the hydrazide to form the acyl azide which serves as acylating agent,

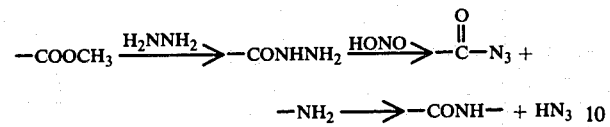

$$-\text{NH}_2 \longrightarrow -\text{CONH}- + \text{HN}_3$$

Le

In these various ways artifical antigens are prepared by coupling the synthesized determinants to soluble carrier macromolecules such as the proteins bovine serum albumin (BSA) human serum albumin (HSA) and polylysine, to red blood cells, and to polysaccharides such as aminated dextran. Also, immunoabsorbants are prepared using solid supports such as aminated sepharose, aminated polystyrene, polyvinylamine, aminated polyvinylalcohol, aminated polyacrylamide and aminated glass. These solids normally are employed as beads or latex particles but may be used on surfaces of tubes and plates depending on the use for the antigenic surface; that is, as an insoluble absorbant for the extraction of antibodies, for the preparation of an affinity chromatographic column, for the detection of agglutination-type phenomena as for spot tests on surfaces, etc.

The artifical antigens reported in Examples XII to XVI were tested by administration to experimental animals; mainly rabbits and goats. For rabbits the immunization protocol was that described by Martineau[8] and for goats that of Marcus and Grollman.[9] The course of the immunization was followed by quantitative precipitin tests on samples of blood withdrawn at various times. The procedures used were all standard to the field of immunology.[10]

EXAMPLE XII

The antigen ($\beta$-D-gal-O(CH$_2$)$_8$CONH)$_{24}$-BSA (12).

Compound 1 (1 g) was dissolved in a mixture of ethanol (5 ml) and 85% hydrazine hydrate (2 ml). After 24 h the solvent was evaporated and residual traces of hydrazine removed by co-evaporation with toluene to give 8-hydrazinocarbonyloctyl $\beta$-D-galactopyranoside as a white solid which was recrystallized from ethanol, mp 194°, $[\alpha]_D^{18} - 2.16°$ (c 1.1, water) 92% yield.

The hydrazide (88 mg, 0.25 mmol) was dissolved in DMF (3 ml) and the solution cooled to $-25°$. A 3.3 N solution of hydrogen chloride in dioxane (0.33 ml) was added and then tert-butyl nitrite (36 mg, 0.35 mmol) in DMF (0.1 ml). After 30 min, sulfamic acid (20 mg) was added and the stirring was contained for 15 minutes. The acyl azide solution was then added directly to a 0° solution of bovine serum albumin (BSA) (300 mg) dissolved in an aqueous solution 0.08 M in Na$_2$B$_4$O$_4$ and 0.35 M in KHCO$_3$. The pH of the solution remained between 9.05 and 9.30 during the course of the addition. After 16 h the solution was dialyzed against water and freeze dried to provide antigen 12 (310 mg) as a white powder. Incorporation of galactose was determined by the phenol sulfuric acid method and calculated to be 24 moles galactose per mole of BSA.

A group of six San Juan rabbits were immunized with antigen 12 incorporated into Freund's complete adjuvant (FCA). The amount of conjugate administered and the immunization schedule followed the protocol described by Martineau et al.[8] Antibody levels upon completion of the schedule ranged from 178 to 396 $\mu$g per 50 $\mu$l of sera with the average being 277 $\mu$g per 50 $\mu$l sera.

That the antibodies raised to this conjugate are directed mainly toward the $\beta$-galactopyranoside portion of the antigen was demonstrated by measuring the maximum amount of antibody precipitated by three antigens 12, ($\alpha$-D-gal-O(CH$_2$)$_8$CONH)$_{17}$-BSA, and BSA. Typically for 50 $\mu$l of crude sera the results were as follows: antigen 12, 396 $\mu$g; ($\alpha$-D-gal-O(CH$_2$)$_8$CONH)$_{17}$-BSA, 87 $\mu$g; and BSA, 87 $\mu$g. Thus, it is possible to conclude that the greatest portion of the antibody population recognizes specifically the $\beta$-D-gal portion of the hapten. This conclusion is reinforced by inhibition experiments which show that while methyl $\beta$-D-galactopyranoside gives 50% inhibition of precipitation [using ($\beta$-D-gal-O(CH$_2$)$_8$CONH)$_{23}$-HSA as the precipitating antigen] at a concentration of 0.83 $\mu$M/ml, compounds having similar structures require much larger concentrations to be effective; i.e. galactose require 6.6 $\mu$M/ml; methyl $\alpha$-D-galactopyranoside require 33 $\mu$M/ml; lactose require 70 $\mu$M/ml and methyl $\beta$-D-glucopyranoside gives approximately no inhibition.

EXAMPLE XIII

The antigen ($\beta$-D-glcNAc-O(CH$_2$)$_8$CONH)$_{25}$-BSA (13).

This antigen was prepared from the hydrazide derivative of compound 2 using the acyl azide coupling method described in example XII. Sera obtained from rabbits immunized with 13 showed a high specificity for antigens containing the $\beta$-D-glcNAc hapten. Proof of the hapten specific nature of the response comes from hapten specific inhibition of precipitation between 13 and antisera raised to 13. Typically, methyl $\beta$-D-glcNAc gave inhibition of precipitation in the range of 60–80%, while methyl $\beta$-D-galNAc and methyl $\beta$-D-glc virtually no inhibition at the concentration that methyl $\beta$-D-glcNAc was effective.

EXAMPLE XIV

The Lewis-a antigens

Compound 8 (1 g) was dissolved in 85% hydrazine hydrate (4 ml) and allowed to stand for 4 h at ambient temperature. The reaction mixture was diluted with 95% ethanol (20 ml) and the solvents evaporated. The residue was dissolved in 10 ml water and dialyzed against 5 changes of water in an ultrafiltration cell. Lyophilization of the water gave 8-hydrazinocarbonyloctyl 2-acetamido-2-deoxy-4-O-($\alpha$-L-fucopyranosyl)-3-O-($\beta$-D-galactopyranosyl)-$\beta$-D-glucopyranoside (14) in quantitative yield as an amorphous solid, $[\alpha]_D - 72.8°$ (c 1.0, water). This compound and the 5-hydrazinocarbonylpentyl analog were used to prepare the following Lewis-a antigens [Le$^a$-O(CH$_2$)$_8$CONH]$_n$-BSA where n can have any of the following values 11, 22, 30, or 45; [Le$^a$-O(CH$_2$)$_8$CONH]$_{28}$-HSA; [Le$^a$-O(CH$_2$)$_8$CONH]$_{15}$-polylysine; [Le$^a$-O(CH$_2$)$_8$CONH(CH$_2$)$_2$NH]$_{10}$-dextran; [Le$^a$-O(CH$_2$)$_5$CONH]$_n$-BSA where n was 10 or 30; [Le$^a$-O(CH$_2$)$_5$CONH]$_{25}$-HSA by the acyl azide method (cf example XIII). The abbreviation Le$^a$ as used above stands for the Lewis-a trisaccharide determinant:

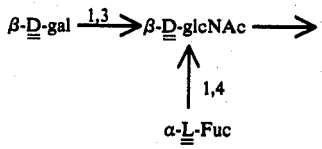

Goat antiserum prepared against the natural Lewis-a blood group substance was found to form a precipitate with the above Le$^a$ antigens.

Using the above Le$^a$ antigens it was possible to examine the effect of factors such as length of the bridging arm and level of hapten incorporation on the immune response to raise antisera specific for the Lewis-a blood group. Antibody levels of sera raised in rabbits to the Le$^a$-BSA antigens possessing C$_6$ and C$_9$ aglyconic "bridging arms" suggest very little variation due to the 3 methylene difference between the two antigens, especially at incorporations of 30 haptens/mole of BSA. At 11 haptens/mole of BSA the Le$^a$-BSA antigen with a C$_9$ bridging arm gave titers averaging about 50% higher than the C$_6$ analog. The level of hapten incorporation also affected antibody production. For rabbits it appeared that an incorporation of about 22 moles of hapten/mole of BSA gave an optimum response in terms of antibody level and specificity. At lower levels of hapten incorporation (~11 moles/mole BSA) increasing amounts of antibody in the sera had a specificity for the carrier, while at higher levels of incorporation (~30 moles/mole BSA) antibody titers were generally lower.

The specificity of the antisera was demonstrated by immunodiffusion reactions. Rabbit antisera raised to Le$^a$-BSA antigens showed a strong line of precipitation with all the artificial Le$^a$ antigens and the natural Lewis-a blood group substance and a very weak line of precipitation was shown with BSA. No line of precipitation was seen with HSA, polylysine or dextran.

To further explore the extent of cross reactions between antibodies raised to the artificial Le$^a$ antigens and human Lewis-a blood group substance and to obtain larger amounts of antisera, a goat was immunized with [Le$^a$-O(CH$_2$)$_8$CONH]$_{30}$-BSA. The antisera obtained showed the expected cross-reaction with human Lewis-a blood group substance and after appropriate treatment effectively agglutinated human blood group Lewis-(a+b−) red cells and did not agglutinate Lewis (a−) red cells. The goat preimmune sea treated in the same manner did not agglutinate Lewis-a red cells.

EXAMPLE XV

The H(O) antigens.

Artificial antigens bearing the H(O) determinant

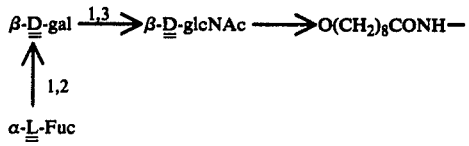

were prepared from compound 9 by the methods described in example XIV. Five rabbits underwent immunization with the anitgen [H(O)]$_{22}$-BSA. On immunodiffusion, the antisera reacted weakly with BSA but strongly with the artificial antigens and human H substance.

Goat antisera were prepared against the natural blood substance H. The artificial antigen was found to form a precipitate with the resulting antiserum when tested by immunodiffusion. Thus, it is apparent antiserum specific for the terminal trisaccharide unit of the type I H-determinant was successfully raised.

EXAMPLE XVI

The B antigens.

Artificial antigens bearing the B determinant

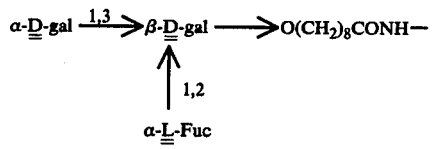

were prepared from compound 10 by the methods described in example XIV. It was found that the artificial B antigens strongly inhibited agglutination of B cells by human anti-B sera. Goat antisera prepared against the natural blood group B substance was found to form a precipitate with the artificial B antigens.

EXAMPLE XVII

Lewis-a immunoabsorbants.

Porous glass beads (100–200 mesh, nominal exclusion limit 1000 Å) were "aminated" using 3-aminopropyltriethoxysilane under standard conditions.[11] The amine content was 69 μM per gram as estimated by the procedure of Esko et al.[12]

The Lewis-a hapten precursor (10 mg, 14.3 μM) (8-hydrazinocarbonyloctyl 2-acetamido-2-deoxy-4-O-(α-L-fucopyranosyl)-3-O-(β-D-galactopyransoyl)-β-D-glucopyranoside) was converted to acyl azide (cf example XIV) for coupling to 5 g of the "aminated" glass beads. The excess amino groups were then acetylated by treatment for 20 min at room temperature with 5% acetic anhydride in aqueous saturated sodium bicarbonate. The beads were then washed with water and air dried to provide immunoabsorbant GB-Le$^a$-1.

When GB-Le$^a$-1 (50 mg) was added to 250 μl of anti-Le$^a$-BSA rabbit serum, the absorption of Le$^a$ antibody was complete within 30 min as estimated by immunodiffusion. Using 25 mg of the absorbant, the antibody removal took near 3 hours. With 10 mg, a small amount of residual antibody could be detected after 5 hours.

The above antiserum had been raised against the artificial Lewis-a anitgen [Le$^a$-O(CH$_2$)$_8$CONH]$_{30}$-BSA. The maximum precipitation against [Le$^a$-O(CH$_2$)$_8$CONH]$_{28}$-HSA as test antigen was 277 μg of antibody per 50 μl of antiserum.

The immunoabsorbant GB-Le$^a$-1 was also tested against an anti-Lewis-a serum raised in a goat using natural Lewis-a blood group substance. The presence of 60 mg of the absorbant in 250 μl of this antiserum caused disappearance of the antibody in the supernatent serum in less than 45 min.

No discernible antibody absorption occurred when N-acetylated "aminated" glass beads were used as control.

EXAMPLE XVIII

H(O) immunoabsorbants.

An immunoabsorbant specific for anti-H antibodies was prepared by coupling compound 9 to glass beads (cf example XVII). This immunoabsorbant was able to absorb from sera antibodies raised to both artificial H antigens and natural H substance.

EXAMPLE XIX

B immunoabsorbants

An immunoabsorbant specific for anti-B antibodies was prepared by coupling compound 10 to glass beads (cf example XVII). This immunoabsorbant (GB-B-1) was able to absorb from sera antibodies raised to both artificial B antigens and natural B substance. This immunoabsorbant also removed anti-B antibodies from typing sera.

Using a panel of fresh B cells suspended in saline the test serum gave positive agglutination to a dilution of 1 to 32. Under the same conditions H(O) cells showed no agglutination. The immunoabsorbant, GB-B-1, (50 mg) was added to 250 μl of sera after 45 min 150 μl of sera was withdrawn and tested against B cells suspended in saline. There was no agglutination of the cells indicating the anti-B antibodies had been removed.

No discernible antibody absorption occurred when N-acetylated "aminated" glass beads were used as control.

To prepare a B immunoabsorbant having a polyacrylic support, a resin containing carboxylic acid groups on an acrylic polymer lattice (10 ml) was treated with a mixture of ethylene diamine (21 g), 1-cyclohexyl-3-(2-morpholinoethyl)-carbodiimide metho-p-toluenesulfonate (15 g) in 100 ml of water for 24 h (the pH of the solution was maintained at 5 by the addition of concentrated hydrochloric acid). The resin was filtered off, washed with water and air dried.

N-Ethoxycarbonyl-2-ethoxy-1,2-dihydroquinoline mediated condensation of 8-hydroxycarbonyloctyl 2-O-(α-L-fucopyranosyl)-3-O-α-D-galactopyranosyl-β-D-galactopyranoside (10 μM/ml resin) (prepared from 10 by hydrolysis of the ester) with the "aminated" resin, followed by N-acetylation of the unreacted amino groups gave the desired B immunoabsorbant. This immunoabsorbant also selectively removed anti-B antibodies from B antisera.

A B immunoabsorbant having an agarose matrix was also prepared by condensing 10 with "aminated" agarose.

REFERENCES

1. W. F. Goebel and O. T. Avery, J. Exp. Med., 50, 521 (1929).
2. O. T. Avery and W. F. Goebel, J. Exp. Med., 50, 533 (1929).
3. W. F. Goebel, J. Exp. Med., 64, 29 (1936).
4. V. P. Rege, T. J. Painter, W. M. Watkins, and W. T. J. Morgan, Nature (London), 204, 740 (1964).
5. Y. Arakatsu, G. Ashwell, and E. A. Kabat, J. Immunol., 97, 858 (1966).
6. K. Himmelspach, O. Westphal, and B. Teichmann, Eur. J. Immunol., 1, 106 (1971).
7. R. U. Lemieux, D. R. Bundle, and D. A. Baker, J. Amer. Chem. Soc., 97, 4076 (1975).
8. R. S. Martineau, P. Z. Allen, I. J. Goldstein, R. N. Iyer, Immunochemistry, 8, 705 (1971).
9. D. M. Marcus and A. P. Grollman, J. Immunol., 97, 867 (1966).
10. E. A. Kabat and M. M. Mayer, "Experimental Immunochemistry," 2nd ed., Oliver and Boyd, London, 1967.
11. H. H. Westal and A. M. Filbert, "Methods of Enzymology," 34 (b), 64 (1974).
12. K. Esko, S. Karlson, and J. Porath, Acta Chem. Scand., 22, 3342 (1968).
13. O. Th. Schmidt, Methods in Carbohydrate Chemistry, I, 349 (1962).
14. P. Z. Allen, Methods in Carbohydrate Chemistry, I, 372 (1962).
15. E. A. Talley, Methods in Carbohydrate Chemistry, II, 337 (1963).
16. H. M. Flowers, Methods in Carbohydrate Chemistry, VI, 474 (1972).
17. N. K. Kochetkov and A. F. Bochkov, Methods in Carbohydrate Chemistry, VI, 480 (1972).
18. S. E. Zurabayan, T. S. Antonenko and Ya. Khorlin, Carbohydrate Research, 15, 21 (1970).

We claim:

1. An O-β-glycoside having the general structure

wherein R is an aliphatic hydrocarbon moiety having 3 to 17 carbon atoms and R" is —H, —OH, —NH$_2$, —NHNH$_2$, —N$_3$, or lower alkoxy, and n has a value of 1 to 4.

2. The β-glycoside of claim 1 wherein the aldoses are selected from the group consisting of D-glucose, D-galactose, D-mannose, L-fucose, and 2-acetamido-2-deoxy-D-glucose.

3. The β-glycoside of claim 1 wherein n is two or three and the aldoses present are selected from the group consisting of D-galactose, D-glucosamine and L-fucose.

4. The β-glycoside of claim 1 wherein R is selected from the group consisting of linear aliphatic hydrocarbons of the general structure (CH$_2$)$_n$ where n varies from 5 to 10.

5. The β-glycoside of claim 1 wherein R" is selected from the group —H, —OH, —NHNH$_2$, —N$_3$, —OCH$_3$ and —OCH$_2$CH$_3$.

6. The lower oligosaccharide derivatives of claim 1 where n is 2, 3, or 4 and each additional aldose moiety is O-α- or O-β-glycosidically-linked to the preceding aldose.

7. The oligosaccharide derivative of claim 6 wherein the further attached moieties are O-β-glycosidically-linked.

8. The lower oligosaccharide derivative of claim 6 wherein the further attached moieties are O-α-glycosidically-linked.

* * * * *